(12) United States Patent
Yeh et al.

(10) Patent No.: US 11,557,070 B2
(45) Date of Patent: Jan. 17, 2023

(54) SYSTEM, METHOD, AND COMPUTER PROGRAM PRODUCT FOR GENERATING PRUNED TRACTOGRAMS OF NEURAL FIBER BUNDLES

(71) Applicant: University of Pittsburgh—Of the Commonwealth System of Higher Education, Pittsburgh, PA (US)

(72) Inventors: Fang-Cheng Yeh, Pittsburgh, PA (US); Jessica Valentina Barrios Martinez, Homestead, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 408 days.

(21) Appl. No.: 16/891,362

(22) Filed: Jun. 3, 2020

(65) Prior Publication Data
US 2020/0380740 A1 Dec. 3, 2020

Related U.S. Application Data
(60) Provisional application No. 62/856,299, filed on Jun. 3, 2019.

(51) Int. Cl.
*G06K 9/00* (2022.01)
*A61B 5/05* (2021.01)
(Continued)

(52) U.S. Cl.
CPC .......... *G06T 11/008* (2013.01); *A61B 5/0042* (2013.01); *A61B 5/055* (2013.01);
(Continued)

(58) Field of Classification Search
CPC .................................... G06K 9/00; A61B 5/05
(Continued)

(56) References Cited

U.S. PATENT DOCUMENTS
8,593,142 B2 * 11/2013 Mori ....................... G06T 7/344
324/309
9,488,710 B2 * 11/2016 Boada .................. G01R 33/561
(Continued)

FOREIGN PATENT DOCUMENTS
JP 5475347 B2 4/2014

OTHER PUBLICATIONS
Abhinav et al., "Advanced diffusion MRI fiber tracking in neurosurgical and neurodegenerative disorders and neuroanatomical studies: A review", Biochimica et Biophysica Acta, 2014, pp. 2286-2297, vol. 1842.
(Continued)

*Primary Examiner* — Seyed H Azarian
(74) *Attorney, Agent, or Firm* — The Webb Law Firm

(57) ABSTRACT

Disclosed are a system, method, and computer program product for generating pruned tractograms of neural fiber bundles. The method includes receiving scan data produced by diffusion imaging of at least a portion of a brain from a magnetic-resonance imaging (MRI) device. The method also includes generating an initial tractogram by mapping neuronal fiber pathways of a target fiber bundle of the scan data. The method further includes generating a density map using a set of tracts from the initial tractogram, identifying each tract that passes through a segment of the density map more than once, and setting a contribution of said tract to a unique tract count of the segment equal to a threshold pruning value. The method further includes generating a pruned tractogram by identifying a segment having a unique tract count less than or equal to the threshold pruning value and excluding the segment from the pruned tractogram.

17 Claims, 12 Drawing Sheets
(6 of 12 Drawing Sheet(s) Filed in Color)

(51) Int. Cl.
| | |
|---|---|
| G06T 11/00 | (2006.01) |
| G16H 30/40 | (2018.01) |
| G16H 15/00 | (2018.01) |
| G16H 50/20 | (2018.01) |
| G16H 40/63 | (2018.01) |
| A61B 5/00 | (2006.01) |
| A61B 5/055 | (2006.01) |
| A61B 34/10 | (2016.01) |
| G01R 33/563 | (2006.01) |
| G01R 33/56 | (2006.01) |
| G16H 30/20 | (2018.01) |

(52) U.S. Cl.
CPC ............ *A61B 5/7435* (2013.01); *A61B 34/10* (2016.02); *G01R 33/5608* (2013.01); *G01R 33/56341* (2013.01); *G16H 15/00* (2018.01); *G16H 30/20* (2018.01); *G16H 30/40* (2018.01); *G16H 40/63* (2018.01); *G16H 50/20* (2018.01); *A61B 2034/105* (2016.02); *A61B 2034/107* (2016.02); *G06T 2200/24* (2013.01); *G06T 2210/41* (2013.01)

(58) Field of Classification Search
USPC ....... 382/100, 103, 106, 128–133, 154, 162, 382/172–173, 181, 199, 216, 224, 254, 382/275–276, 285–291, 305; 378/4, 21; 324/309; 600/411, 544
See application file for complete search history.

(56) References Cited

U.S. PATENT DOCUMENTS

| | | | | |
|---|---|---|---|---|
| 9,489,731 | B2* | 11/2016 | Schneider | ............ A61B 5/1075 |
| 9,568,580 | B2* | 2/2017 | Dale | ................ G01R 33/56341 |
| 2009/0016590 | A1 | 1/2009 | Tseng et al. | |
| 2010/0253337 | A1 | 10/2010 | Tseng et al. | |
| 2013/0259340 | A1 | 10/2013 | Tseng et al. | |
| 2017/0052241 | A1* | 2/2017 | Cetingul | .......... G01R 33/56341 |
| 2019/0365273 | A1* | 12/2019 | Jara | ...................... A61B 5/0042 |

OTHER PUBLICATIONS

Abhinav et al., "Application of High-Definition Fiber Tractography in the Management of Supratentorial Cavernous Malformations: A Combined Qualitative and Quantitative Approach", Neurosurgery, 2014, pp. 668-681, vol. 74.

Abhinav et al., "Use of diffusion spectrum imaging in preliminary longitudinal evaluation of amyotrophic lateral sclerosis: development of an imaging biomarker", Frontiers in Human Neuroscience, 2014, 11 pages, vol. 8.

Basser et al., "In Vivo Fiber Tractography Using DT-MRI Data", Magnetic Resonance in Medicine, 2000, pp. 625-632, vol. 44.

Duffau, "Diffusion Tensor Imaging Is a Research and Educational Tool, but Not Yet a Clinical Tool", World Neurosurgery, 2014, 3 pages.

Fernandez-Miranda et al., "Asymmetry, connectivity, and segmentation of the arcuate fascicle in the human brain", Brain Struct Funct, 2014, 16 pages.

Fernandez-Miranda et al., "High-Definition Fiber Tractography of the Human Brain: Neuroanatomical Validation and Neurosurgical Applications", Neurosurgery, 2012, pp. 430-453, vol. 71.

Gangolli et al., "Quantitative validation of a nonlinear histology-MRI coregistration method using generalized Q-sampling imaging in complex human cortical white matter", NeuroImage, 2017, pp. 152-167, vol. 153.

Jbabdi et al., "Measuring macroscopic brain connections in vivo", Nature Neuroscience, 2015, pp. 1546-1555, vol. 18:11.

Maier-Hein, "The challenge of mapping the human connectome based on diffusion tractography", Nature Communications, 2017, 13 pages.

Meola et al., "Human Connectome-Based Tractographic Atlas of the Brainstem Connections and Surgical Approaches", Neurosurgery, 2016, pp. 1-18.

Meola et al., "The Controversial Existence of the Human Superior Fronto-Occipital Fasciculus: Connectome-Based Tractographic Study with Microdissection Validation", Human Brain Mapping, 2015, pp. 4964-4971, vol. 36.

Meola et al., "The nondecussating pathway of the dentatorubrothalamic tract in humans: human connectome-based tractographic study and microdissection validation", J Neurosurg, 2015, 7 pages.

Modo et al., "Detection of Aberrant Hippocampal Mossy Fiber Connections: Ex Vivo Mesoscale Diffusion MRI and Microtractography With Histological Validation in a Patient With Uncontrolled Temporal Lobe Epilepsy", Human Brain Mapping, 2016, pp. 780-795, vol. 37.

Pestilli et al., "Evaluation and statistical inference for living connectomes", Nat Methods, 2014, pp. 1058-1063, vol. 11:10.

Reveley et al., "Superficial white matter fiber systems impede detection of long-range cortical connections in diffusion MR tractography", PNAS, 2015, pp. E2820-E2828.

Smith et al., "Anatomically-contrained tractography: Improved diffusion MRI streamlines tractography through effective use of anatomical information", NeuroImage, 2012, pp. 1924-1938, vol. 62.

Thomas et al., "Anatomical accuracy of brain connections derived from diffusion MRI tractography is inherently limited", PNAS, 2014, pp. 16574-16579, vol. 111:46.

Tournier et al., "Diffusion Tensor Imaging and Beyond", Magn Reson Med, 2011, pp. 1532-1556, vol. 65:5.

"Tractometer by Scil", Tractometer—ISMRM 2015 Tractography Challenge, www.tractometer.org/ismrm_2015_challenge/, 2 pages, Mar. 25, 2022.

Wang et al., "Rethinking the Role of the Middle Longitudinal Fascicle in Language and Auditory Pathways", Cerebral Cortex, 2012, 10 pages.

Wang et al., "Subcomponents and connectivity of the superior longitudinal fasciculus in the human brain", Brain Struct Funt, 2014, 18 pages.

Yeatman et al., "The vertical occipital fasciculus: A century of controversy resolved by in vivo measurements", PNAS Early Edition, 2014, 10 pages.

Yeh et al., "Automatic Removal of False Connections in Diffusion MRI Tractography Using Topology-Informed Pruning (TIP)", Neurotherapeutics, 2018, 7 pages.

Yeh et al., "Deterministic Diffusion Fiber Tracking Improved by Quantitative Anisotropy", PLoS One, 2013, 16 pages, vol. 8:11.

Yeh et al., "Generalized q-Sampling Imaging", IEEE Transactions on Medical Imaging, 2010, pp. 1626-1635, vol. 29:9.

Yeh et al., "Mapping Immune Cell Infiltration Using Restricted Diffusion MRI", Magn Reson Med, 2017, pp. 603-612, vol. 77:2.

Yeh et al., "Population-averaged atlas of the macroscale human structural connectome and its network topology", NeuroImage, 2018, pp. 57-68, vol. 178.

Yoshino et al., "Visualization of Cranial Nerves Using High-Definition Fiber Tractography", Neurosurgery, 2016, pp. 146-165, vol. 79.

\* cited by examiner

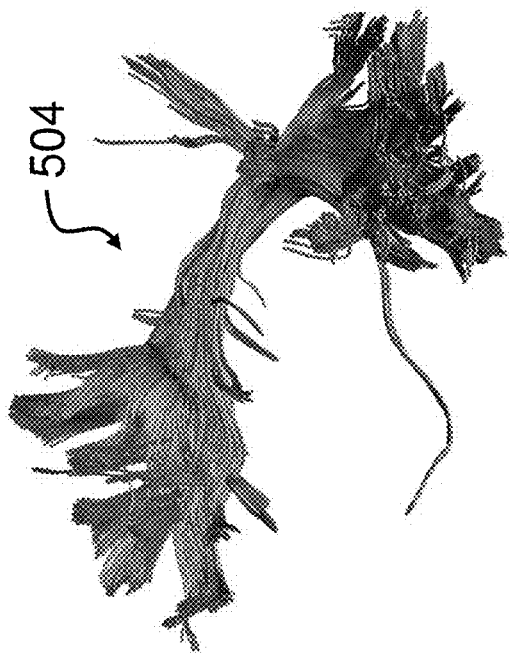
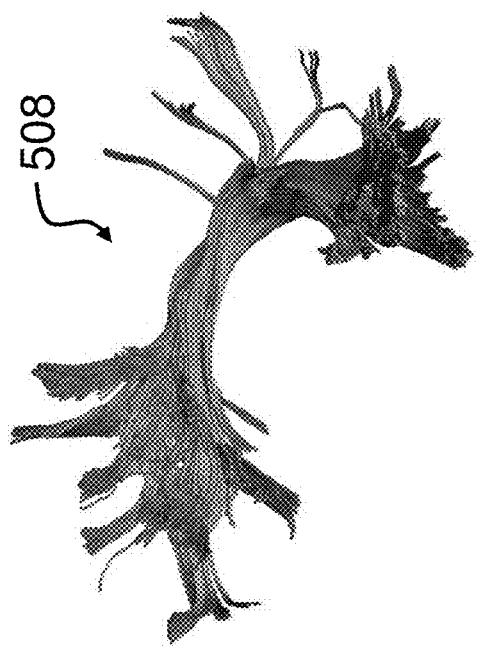
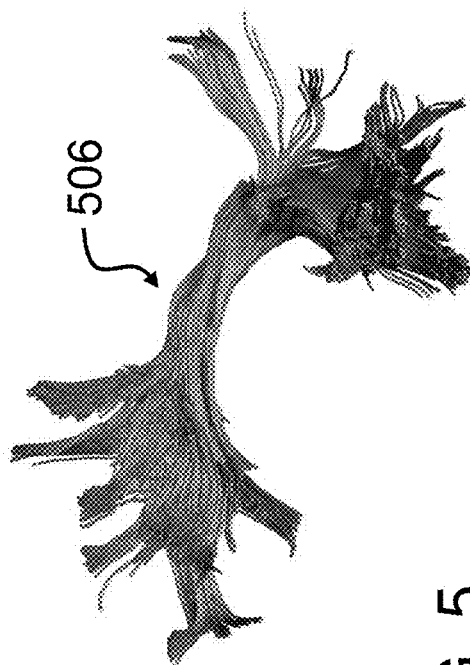
FIG. 5

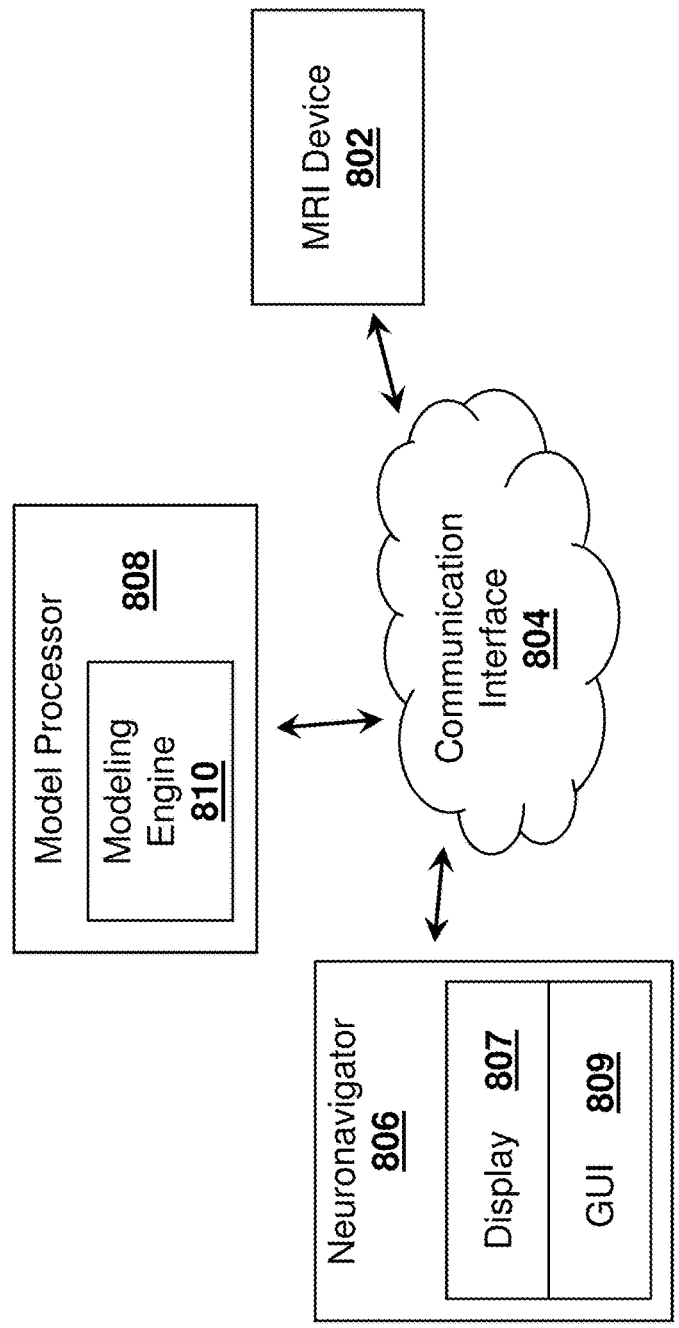

SYSTEM, METHOD, AND COMPUTER PROGRAM PRODUCT FOR GENERATING PRUNED TRACTOGRAMS OF NEURAL FIBER BUNDLES

CROSS-REFERENCE TO RELATED APPLICATIONS

This application claims priority to U.S. Provisional Patent Application No. 62/856,299 titled "High Accuracy Fiber Tracking on Surgical Navigator," filed Jun. 3, 2019, the entire disclosure of which is hereby incorporated by reference in its entirety.

STATEMENT REGARDING FEDERAL FUNDING

This invention was made with government support under Grant No. MH113634 awarded by the National Institutes of Health. The government has certain rights in the invention.

BACKGROUND

Brain tumor removal is difficult, and often leads to severe post-operative complications. Neuronavigation is a magnetic-resonance imaging (MRI) technique used during the brain tumor removal operation to assist the surgeon in identifying the critical (e.g., healthy) tracts of the brain to be avoided. The accuracy of current neuronavigation units is poor.

In the United States, around 25,000 adults are diagnosed with a brain tumor every year (males 5.8, females 4.1 per 100,000). At the University of Pittsburgh Medical Center (UPMC), the Neurological Surgery Department treats an average of 500 brain tumor patients per year. Surgical removal of the tumor is offered in 95% of cases, but favorable outcomes to the surgical approach are affected by limitations in imaging modalities during surgery. Patients who undergo brain tumor surgery often have significant postsurgical complications, including motor deficits and cognitive impairment, and do not recover to their full pre-surgical extent. Therefore there is a need for an improved tractogram generation solution providing a safer approach to prevent these complications.

SUMMARY

Non-limiting embodiments port HAFT data to surgical navigation systems using a super-resolution conversion from track file format to voxel format. Described systems and methods re-grid the HAFT space into smaller voxel elements to obtain high quality and super-resolution quality of the maps, which allow neurosurgeons to perform brain tumor surgery with high definition visualization of fiber tracts involved and surrounding the lesion. Non-limiting embodiments generate more accurate tractograms by pruning false connections (e.g., singular tracts) from segments of density maps of scanned MRI data. Accordingly, systems, devices, products, apparatus, and/or methods for generating pruned tractograms of neural fiber bundles are provided herein.

According to a non-limiting embodiment or aspect, provided is a computer-implemented method for generating pruned tractograms of neural fiber bundles. The method includes receiving, with at least one processor, scan data produced by diffusion imaging of at least a portion of a brain from a magnetic-resonance imaging (MRI) device. The method also includes generating, with the at least one processor, an initial tractogram by mapping neuronal fiber pathways of a target fiber bundle of the scan data. The method further includes generating, with the at least one processor, a density map of the at least a portion of the brain using a set of tracts from the initial tractogram. The method further includes identifying, with the at least one processor, each tract of the set of tracts that passes through a segment of a plurality of segments of the density map more than once, and setting a contribution of said tract to a unique tract count of the segment equal to a threshold pruning value. The method further includes generating, with the at least one processor, a pruned tractogram from the initial tractogram by identifying at least one segment of the plurality of segments having a unique tract count less than or equal to the threshold pruning value and excluding the at least one segment from the pruned tractogram. The method further includes communicating, with the at least one processor, the pruned tractogram for display on a computing device.

In non-limiting embodiments or aspects, the computing device may include a neuronavigator device programmed and/or configured to use the pruned tractogram in a computer-aided surgical process of the brain to avoid affecting a critical neural pathway of the brain.

In non-limiting embodiments or aspects, the density map may be a three-dimensional (3D) histogram and the plurality of segments may be a plurality of voxels of the 3D histogram. The pruned tractogram may include only voxels having unique tract counts greater than the threshold pruning value, and the threshold pruning value may be one.

In non-limiting embodiments or aspects, the method may further include generating, with the at least one processor, a second density map of the at least a portion of the brain using a second set of tracts from the initial tractogram. The method may further include identifying, with the at least one processor, each tract of the second set of tracts that passes through a segment of a plurality of segments of the second density map more than once, and setting a contribution of said tract to a unique tract count of the segment of the plurality of segments of the second density map equal to the threshold pruning value. The method may further include generating, with the at least one processor, an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram. The pruned tractogram may be generated at least partially from the intermediate tractogram.

In non-limiting embodiments or aspects, the method may further include displaying, with the at least one processor, the pruned tractogram in a graphical user interface. The method may further include receiving, with the at least one processor, input data from a user including additional tracts for removal from the pruned tractogram. The method may further include modifying, with the at least one processor, the pruned tractogram based on the input data. The computing device may include a neuronavigator device programmed and/or configured to use the pruned tractogram in a computer-aided surgical process of the brain to avoid affecting a critical neural pathway of the brain.

According to a non-limiting embodiment or aspect, provided is a computer program product for generating pruned tractograms of neural fiber bundles. The computer program product includes at least one non-transitory computer-readable medium including program instructions that, when executed by at least one processor, cause the at least one processor to receive scan data produced by diffusion imaging of at least a portion of a brain from a magnetic-resonance imaging (MRI) device. The program instructions also cause the at least one processor to generate an initial tractogram by mapping neuronal fiber pathways of a target fiber bundle of the scan data. The program instructions further cause the at least one processor to generate a density map of the at least a portion of the brain using a set of tracts from the initial tractogram. The program instructions further cause the at least one processor to identify each tract of the set of tracts that passes through a segment of a plurality of segments of the density map more than once, and set a contribution of said tract to a unique tract count of the segment equal to a threshold pruning value. The program instructions further cause the at least one processor to generate a pruned tractogram from the initial tractogram by identifying at least one segment of the plurality of segments having a unique tract count less than equal to the threshold pruning value and excluding the at least one segment from the pruned tractogram. The program instructions further cause the at least one processor to communicate the pruned tractogram for display on a computing device.

In non-limiting embodiments or aspects, the computing device may include a neuronavigator device programmed and/or configured to use the pruned tractogram in a computer-aided surgical process of the brain to avoid affecting a critical neural pathway of the brain.

In non-limiting embodiments or aspects, the density map may be a three-dimensional (3D) histogram and the plurality of segments are a plurality of voxels of the 3D histogram. The pruned tractogram may include only voxels having unique tract counts greater than the threshold pruning value, and the threshold pruning value may be one.

In non-limiting embodiments or aspects, the program instructions may further cause the at least one processor to generate a second density map of the at least a portion of the brain using a second set of tracts from the initial tractogram. The program instructions may further cause the at least one processor to identify each tract of the second set of tracts that passes through a segment of a plurality of segments of the second density map more than once, and setting a contribution of said tract to a unique tract count of the segment of the plurality of segments of the second density map equal to the threshold pruning value. The program instructions may further cause the at least one processor to generate an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram. The pruned tractogram may be generated at least partially from the intermediate tractogram.

In non-limiting embodiments or aspects, the program instructions may further cause the at least one processor to display the pruned tractogram in a graphical user interface. The program instructions may further cause the at least one processor to receive input data from a user including additional tracts for removal from the pruned tractogram. The program instructions may further cause the at least one processor to modify the pruned tractogram based on the input data. The computing device may include a neuronavigator device programmed and/or configured to use the pruned tractogram in a computer-aided surgical process of the brain to avoid affecting a critical neural pathway of the brain.

According to a non-limiting embodiment or aspect, provided is a system for generating pruned tractograms of neural fiber bundles. The system includes a neuronavigator device including at least one processor that is programmed and/or configured to receive scan data produced by diffusion imaging of at least a portion of a brain from a magnetic-resonance imaging (MRI) device. The at least one processor is also programmed and/or configured to generate an initial tractogram by mapping neuronal fiber pathways of a target fiber bundle of the scan data. The at least one processor is further programmed and/or configured to generate a density map of the at least a portion of the brain using a set of tracts from the initial tractogram. The at least one processor is further programmed and/or configured to identify each tract of the set of tracts that passes through a segment of a plurality of segments of the density map more than once, and set a contribution of said tract to a unique tract count of the segment equal to a threshold pruning value. The at least one processor is further programmed and/or configured to generate a pruned tractogram from the initial tractogram by identifying at least one segment of the plurality of segments having a unique tract count less than or equal to the threshold pruning value and excluding the at least one segment from the pruned tractogram. The at least one processor is further programmed and/or configured to display the pruned tractogram.

In non-limiting embodiments or aspects, the at least one processor may be further programmed and/or configured to use the pruned tractogram in a computer-aided surgical process of the brain to avoid affecting a critical neural pathway of the brain.

In non-limiting embodiments or aspects, the density map may be a three-dimensional (3D) histogram and the plurality of segments may be a plurality of voxels of the 3D histogram. The pruned tractogram may include only voxels having unique tract counts greater than the threshold pruning value, and the threshold pruning value may be one.

In non-limiting embodiments or aspects, the at least one processor may be further programmed and/or configured to generate a second density map of the at least a portion of the brain using a second set of tracts from the initial tractogram. The at least one processor may be further programmed and/or configured to identify each tract of the second set of tracts that passes through a segment of a plurality of segments of the second density map more than once, and setting a contribution of said tract to a unique tract count of the segment of the plurality of segments of the second density map equal to the threshold pruning value. The at least one processor may be further programmed and/or configured to generate an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram. The pruned tractogram may be generated at least partially from the intermediate tractogram.

In non-limiting embodiments or aspects, the at least one processor may be further programmed and/or configured to display the pruned tractogram in a graphical user interface. The at least one processor may be further programmed and/or configured to receive input data from a user including additional tracts for removal from the pruned tractogram. The at least one processor may be further programmed and/or configured to modify the pruned tractogram based on the input data. The at least one processor may be further programmed and/or configured to use the pruned tractogram in a computer-aided surgical process of the brain to avoid affecting a critical neural pathway of the brain.

Other non-limiting embodiments or aspects are set forth in the following numbered clauses:

Clause 1: A computer-implemented method comprising: receiving, with at least one processor, scan data produced by diffusion imaging of at least a portion of a brain from a magnetic-resonance imaging (MRI) device; generating, with the at least one processor, an initial tractogram by mapping neuronal fiber pathways of a target fiber bundle of the scan data; generating, with the at least one processor, a density map of the at least a portion of the brain using a set of tracts from the initial tractogram; identifying, with the at least one processor, each tract of the set of tracts that passes through a segment of a plurality of segments of the density map more than once, and setting a contribution of said tract to a unique tract count of the segment equal to a threshold pruning value; generating, with the at least one processor, a pruned tractogram from the initial tractogram by identifying at least one segment of the plurality of segments having a unique tract count less than or equal to the threshold pruning value and excluding the at least one segment from the pruned tractogram; and communicating, with the at least one processor, the pruned tractogram for display on a computing device.

Clause 2: The computer-implemented method of clause 1, wherein the computing device comprises a neuronavigator device programmed and/or configured to use the pruned tractogram in a computer-aided surgical process of the brain to avoid affecting a critical neural pathway of the brain.

Clause 3: The computer-implemented method of clause 1 or 2, wherein the density map is a three-dimensional (3D) histogram and the plurality of segments are a plurality of voxels of the 3D histogram.

Clause 4: The computer-implemented method of any of clauses 1-3, wherein the pruned tractogram comprises only voxels having unique tract counts greater than the threshold pruning value, and wherein the threshold pruning value is one.

Clause 5: The computer-implemented method of any of clauses 1-4, further comprising: generating, with the at least one processor, a second density map of the at least a portion of the brain using a second set of tracts from the initial tractogram; identifying, with the at least one processor, each tract of the second set of tracts that passes through a segment of a plurality of segments of the second density map more than once, and setting a contribution of said tract to a unique tract count of the segment of the plurality of segments of the second density map equal to the threshold pruning value; and generating, with the at least one processor, an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram, wherein the pruned tractogram is generated at least partially from intermediate tractogram.

Clause 6: The computer-implemented method of any of clauses 1-5, further comprising: displaying, with the at least one processor, the pruned tractogram in a graphical user interface; receiving, with the at least one processor, input data from a user comprising additional tracts for removal from the pruned tractogram; and modifying, with the at least one processor, the pruned tractogram based on the input data.

Clause 7: The computer-implemented method of any of clauses 1-6, wherein the computing device comprises a neuronavigator device programmed and/or configured to use the pruned tractogram in a computer-aided surgical process of the brain to avoid affecting a critical neural pathway of the brain.

Clause 8: A computer program product comprising at least one non-transitory computer-readable medium including program instructions that, when executed by at least one processor, cause the at least one processor to: receive scan data produced by diffusion imaging of at least a portion of a brain from a magnetic-resonance imaging (MRI) device; generate an initial tractogram by mapping neuronal fiber pathways of a target fiber bundle of the scan data; generate a density map of the at least a portion of the brain using a set of tracts from the initial tractogram; identify each tract of the set of tracts that passes through a segment of a plurality of segments of the density map more than once, and set a contribution of said tract to a unique tract count of the segment equal to a threshold pruning value; generate a pruned tractogram from the initial tractogram by identifying at least one segment of the plurality of segments having a unique tract count equal to the threshold pruning value and excluding the at least one segment from the pruned tractogram; and communicate the pruned tractogram for display on a computing device.

Clause 9: The computer program product of clause 8, wherein the computing device comprises a neuronavigator device programmed and/or configured to use the pruned tractogram in a computer-aided surgical process of the brain to avoid affecting a critical neural pathway of the brain.

Clause 10: The computer program product of clause 8 or 9, wherein the density map is a three-dimensional (3D) histogram and the plurality of segments are a plurality of voxels of the 3D histogram.

Clause 11: The computer program product of any of clauses 8-10, wherein the pruned tractogram comprises only voxels having unique tract counts greater than the threshold pruning value, and wherein the threshold pruning value is one.

Clause 12: The computer program product of any of clauses 8-11, wherein the program instructions further cause the at least one processor to: generate a second density map of the at least a portion of the brain using a second set of tracts from the initial tractogram; identify each tract of the second set of tracts that passes through a segment of a plurality of segments of the second density map more than once, and setting a contribution of said tract to a unique tract count of the segment of the plurality of segments of the second density map equal to the threshold pruning value; and generate an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram, wherein the pruned tractogram is generated at least partially from the intermediate tractogram.

Clause 13: The computer program product of any of clauses 8-12, wherein the program instructions further cause the at least one processor to: display the pruned tractogram in a graphical user interface; receive input data from a user comprising additional tracts for removal from the pruned tractogram; and modify the pruned tractogram based on the input data.

Clause 14: The computer program product of any of clauses 8-13, wherein the computing device comprises a neuronavigator device programmed and/or configured to use the pruned tractogram in a computer-aided surgical process of the brain to avoid affecting a critical neural pathway of the brain.

Clause 15: A system comprising a neuronavigator device comprising at least one processor that is programmed and/or configured to: receive scan data produced by diffusion imaging of at least a portion of a brain from a magnetic-resonance imaging (MRI) device; generate an initial tractogram by mapping neuronal fiber pathways of a target fiber bundle of the scan data; generate a density map of the at least a portion of the brain using a set of tracts from the initial tractogram; identify each tract of the set of tracts that passes through a segment of a plurality of segments of the density map more than once, and set a contribution of said tract to a unique tract count of the segment equal to a threshold pruning value; generate a pruned tractogram from the initial tractogram by identifying at least one segment of the plurality of segments having a unique tract count less than or equal to the threshold pruning value and excluding the at least one segment from the pruned tractogram; and display the pruned tractogram.

Clause 16: The system of clause 15, wherein the at least one processor is further programmed and/or configured to use the pruned tractogram in a computer-aided surgical process of the brain to avoid affecting a critical neural pathway of the brain.

Clause 17: The system of clause 15 or 16, wherein the density map is a three-dimensional (3D) histogram and the plurality of segments are a plurality of voxels of the 3D histogram.

Clause 18: The system of any of clauses 15-17, wherein the pruned tractogram comprises only voxels having unique tract counts greater than the threshold pruning value, and wherein the threshold pruning value is one.

Clause 19: The system of any of clauses 15-18, wherein the at least one processor is further programmed and/or configured to: generate a second density map of the at least a portion of the brain using a second set of tracts from the initial tractogram; identify each tract of the second set of tracts that passes through a segment of a plurality of segments of the second density map more than once, and setting a contribution of said tract to a unique tract count of the segment of the plurality of segments of the second density map equal to the threshold pruning value; and generate an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram, wherein the pruned tractogram is generated at least partially from the intermediate tractogram.

Clause 20: The system of any of clauses 15-19, wherein the at least one processor is further programmed and/or configured to: display the pruned tractogram in a graphical user interface; receive input data from a user comprising additional tracts for removal from the pruned tractogram; modify the pruned tractogram based on the input data; and use the pruned tractogram in a computer-aided surgical process of the brain to avoid affecting a critical neural pathway of the brain.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Additional advantages and details are explained in greater detail below with reference to the non-limiting, exemplary embodiments that are illustrated in the accompanying figures, in which:

FIG. 5 illustrates tractograms comparing manual pruning by experts to systems and methods of generating pruned tractograms of neural fiber bundles according to non-limiting embodiments;

FIG. 8 is a schematic diagram of a system for generating pruned tractograms of neural fiber bundles according to non-limiting embodiments;

DESCRIPTION OF THE PREFERRED EMBODIMENTS

Figure 1B:
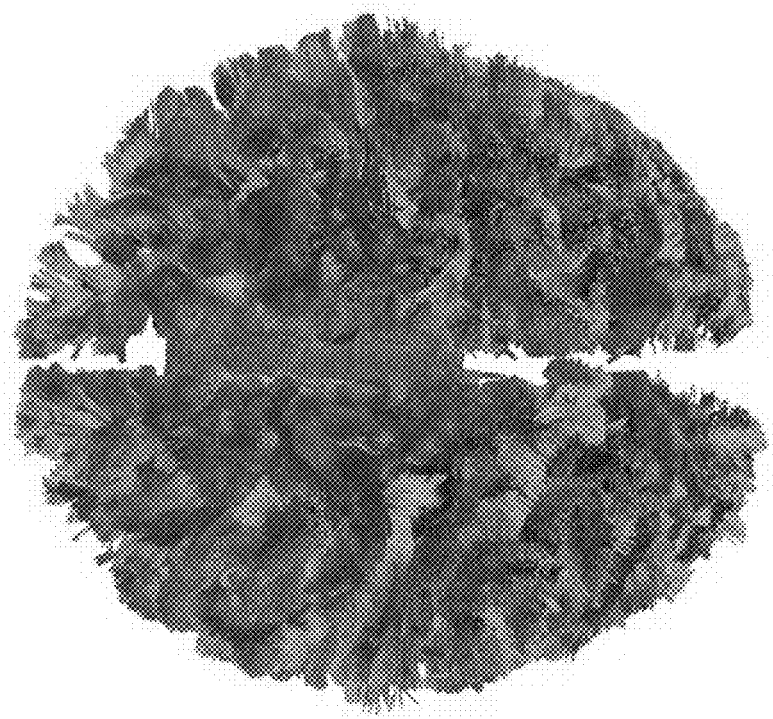
FIG. 1B illustrates a prior art total-brain tractogram generated using a HAFT process.

For purposes of the description hereinafter, the terms "end," "upper," "lower," "right," "left," "vertical," "horizontal," "top," "bottom," "lateral," "longitudinal," and derivatives thereof shall relate to the embodiments as they are oriented in the drawing figures. However, it is to be understood that the embodiments may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects disclosed herein are not to be considered as limiting.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, and/or the like) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the term "communication" may refer to the reception, receipt, transmission, transfer, provision, and/or the like, of data (e.g., information, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit processes information received from the first unit and communicates the processed information to the second unit.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. As an example, a mobile device may include a cellular phone (e.g., a smartphone or standard cellular phone), a portable computer, a wearable device (e.g., watches, glasses, lenses, clothing, and/or the like), a personal digital assistant (PDA), and/or other like devices. A computing device may also be a desktop computer or other form of non-mobile computer. A computing device may include a computer program product, e.g., one or more non-transitory computer-readable data storage media programmed and/or configured to store program instructions that, when executed by one or more processors, cause one or more processors to execute a computer function.

As used herein, the term "server" may refer to or include one or more computing devices that are operated by or facilitate communication and processing for multiple parties in a network environment, such as the Internet, although it will be appreciated that communication may be facilitated over one or more public or private network environments and that various other arrangements are possible. Further, multiple computing devices (e.g., servers, mobile devices, etc.) directly or indirectly communicating in the network environment may constitute a "system." Reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

As used herein, the term "graphical user interface" (GUI) refers to a generated display, such as one or more displays with which a user may interact, either directly or indirectly (e.g., through a keyboard, mouse, touchscreen, etc.).

Every brain tumor surgery offers a unique challenge. The surgical approach that the surgeon takes in a brain tumor surgery depends on the location of the tumor and the displacement of critical neuronal pathways around the tumor. To avoid damaging important fiber pathways (e.g., motor, sensory, language, etc.), neurosurgeons have used surgical navigators, e.g., neuronavigators, to inform brain structure in the operation room. However, current surgical navigators use conventional structural imaging, which does not provide trajectories for important fiber pathways. Neurosurgeons also use diffusion tensor imaging (DTI), but that approach is limited by its accuracy, known to exhibit 40% error in mapping fiber trajectories.

DTI is the MRI-based technology available in current surgical navigators. DTI has several limitations, which impacts the accuracy of surgery and safety of patients. DTI acquires only 30 or 60 sampling directions at only one diffusion sensitization, and a weak gradient coil only at 2.5 mm. The existing DTI methods model diffusion patterns as simple Gaussian distributions. DTI requires 30-60 diffusion gradient samplings to calculate the diffusion tensor, and the axonal direction can be determined by the principal direction of the tensor. Based on this principal direction, the trajectories of the axonal connections can be tracked by diffusion fiber tracking. However, the Gaussian model is considered inadequate in real-world applications because more than 90% of the human brain volume has complicated fiber geometry. Results derived from DTI miss a substantial number of important crossing structures and sometimes create false connections due to tracking failure in the crossing regions, which can lead to even worse consequences.

High Accuracy Fiber Tracking (HAFT) is an MRI neuronavigation software platform and method used for intraoperative MRI neuronavigation that has significantly greater imaging accuracy than other solutions (e.g., DTI: ~40% error, HAFT: ~8% error), allowing for the critical pathways of the brain to be left undamaged leading to reduced post-operative complications during brain tumor removal surgery. Reduced patient complications leads to reduced health care costs. HAFT is a technology that implements a high-sampling-diffusion MRI scan that is modeled by a nonparametric diffusion distribution that guides a fiber tracking algorithm. The approach that this technology uses improves the mapping accuracy of neuronavigators used for brain tumor surgeries.

HAFT pushes the limitation of diffusion MRI to acquire 258 diffusion sampling directions at 23 different sensitization strengths. This high angular resolution diffusion spectrum acquisition provides a means of acquiring the most detailed diffusion data from tumor patients.

Figure 1A:
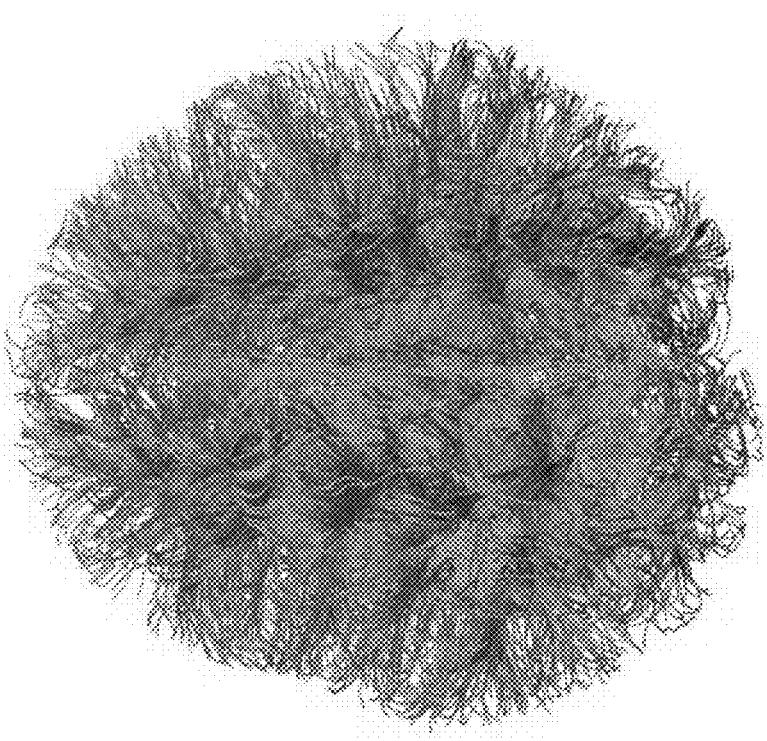
FIG. 1A illustrates a prior art total-brain tractogram generated using a DTI process.

The superiority of HAFT over the commonly used DTI approach has already been demonstrated in several publications. Studies have shown that HAFT (a tractogram therefrom shown in FIG. 1B) is a major improvement over DTI tractography (a tractogram therefrom shown in FIG. 1A) and correlated well with histology and cadaver microdissection in mapping several fiber pathways.

A preliminary study has shown that HAFT can resolve multiple fiber directions, overcome the complexity of the tissue geometry and provide quantitative data, such as track volume and anisotropic diffusion and the total volume of white matter pathways. This white matter information cannot be detected using conventional diffusion tensor imaging (DTI) (compare HAFT, shown in FIG. 1B, to DTI, shown in FIG. 1A). Notwithstanding, tractograms produced by diffusion MRI fiber tracking may include false connections. Fiber bundles may include tracts exhibiting premature termination or false continuity. There is a need in the art for a technical solution to produce enhanced tractograms, such as tractograms having false connections pruned from the generated tractography.

Described systems and methods provide a technical solution referred to herein as topology-informed pruning (TIP), a method that automatically identifies singular tracts and eliminates them to improve neural tracking accuracy. The accuracy of the tractography with and without TIP was evaluated by a team of 6 neuroanatomists in a blinded setting to examine whether TIP could improve the accuracy. The results showed that TIP improved the tracking accuracy by 11.93% in the single-shell scheme and by 3.47% in the grid scheme. The improvement is statistically significantly different from a random pruning (p-value<0.001). The diagnostic agreement between TIP and neuroanatomists was comparable to the agreement between neuroanatomists. The proposed TIP algorithm can be used to automatically clean up noisy fibers in deterministic tractography, with a potential to confirm the existence of a fiber connection in basic neuroanatomical studies or clinical neurosurgical planning.

To understand the improvements in accuracy, it is noted that deterministic tractography may identify false connections. There are two major causes for false connections: premature termination and false continuity. Premature terminations can be partly addressed by using a white matter mask. The mask allows for automatic checking of the fiber trajectory endpoints, and then false endpoints are rejected to achieve a better accuracy. Based on this paradigm, demarcation between white and gray matter boundaries derived from T1-weighted images have been used as a tract-termination benchmark to cope with premature termination problem. False tracts were determined as those prematurely terminating in white rather than gray matter, while real tracts were defined as those which terminated in gray matter, as determined by the overlap of T1 and diffusion-weighted images. However, delineating an accurate white matter mask can be complicated by image distortion in addition to the resolution mismatch between the diffusion-weighted and T1-weighted images. It is possible that this termination check may introduce another error due to an imperfect white matter mask.

Although premature termination can be detected using a white matter mask, there is no effective strategy to detect false continuity using structural images or diffusion data. This is due to the limitation of diffusion MRI techniques in resolving the exact configuration of crossing fibers, such as bending, fanning, or interdigitating. Diffusion signals cannot alone differentiate these configurations within the voxel space. Described systems and methods relieve the requirement for a priori knowledge of white matter anatomy to validate tractography results against the false continuity issue.

By separating whole-brain trajectories into clusters based on their neighboring distance, it may be shown that clusters with fewer neighboring tracts are more likely to be false connections with false continuity. A track with few neighboring tracts may have a high likelihood of being a false continuity. One potential explanation of this phenomenon is that the false tracts arise between the overlapping boundaries of two real, adjacent fiber bundles. Since this overlapping boundary only forms a touching surface or line between two fiber pathways, it will only allow for a limited number of trajectories to pass through and cause false continuity. Moreover, errors of fiber tracking will accumulate during the tracking process. As a result, the trajectories that pass through the overlapping boundaries tend to have very diverse propagation routes due to the perturbation around the boundaries.

These two unique conditions combined will greatly reduce the chance of a false continuity tract to find a neighboring fiber trajectory. Accordingly, the described systems and methods operate to make use of the concept that a singular tract (e.g., a trajectory with no neighboring tract) has a higher likelihood of being a false continuity connection. This concept underlies the topology-informed pruning (TIP) algorithm, which uses the topology of a tractogram itself to identify candidate false connections for removal. In non-limiting embodiments, false connections may be identified by constructing a 3D tract density histogram to single out voxels with only one track passing through them, then subsequently eliminating those singular tracts to improve the accuracy.

One effect provided by the technology is the decrease of incidence of postsurgical morbidities, such as cognitive and motor deficits, as well as the increase of patient survival. The technology may be implemented with a neuronavigator device (e.g., a computing device used by neurosurgeons to plan and guide the surgical approach allowing access to the brain tumor, also called neuronavigators herein). To this end, patients may benefit in undergoing a surgical procedure that provides a more accurate technology that improves surgical outcomes, and hospitals may reduce costs that are currently directed towards the care of patients that develop postsurgical complications. The improvement in survival outcomes is expected to be directly proportional to the improved capacity of neurosurgeons in accessing distant and complex areas to address existing lesions within the white matter.

Described systems and methods combine HAFT with neuronavigators and new modeling techniques to bridge a technical gap in prior neural pathway tracking solutions. HAFT uses diffusion MRI scans to model the diffusion patterns of critical fiber pathways and maps their trajectories. The trajectory information taken by HAFT is then supplied to the surgical navigator, allowing neurosurgeons to know where the critical pathways are during the surgery.

Figure 2:
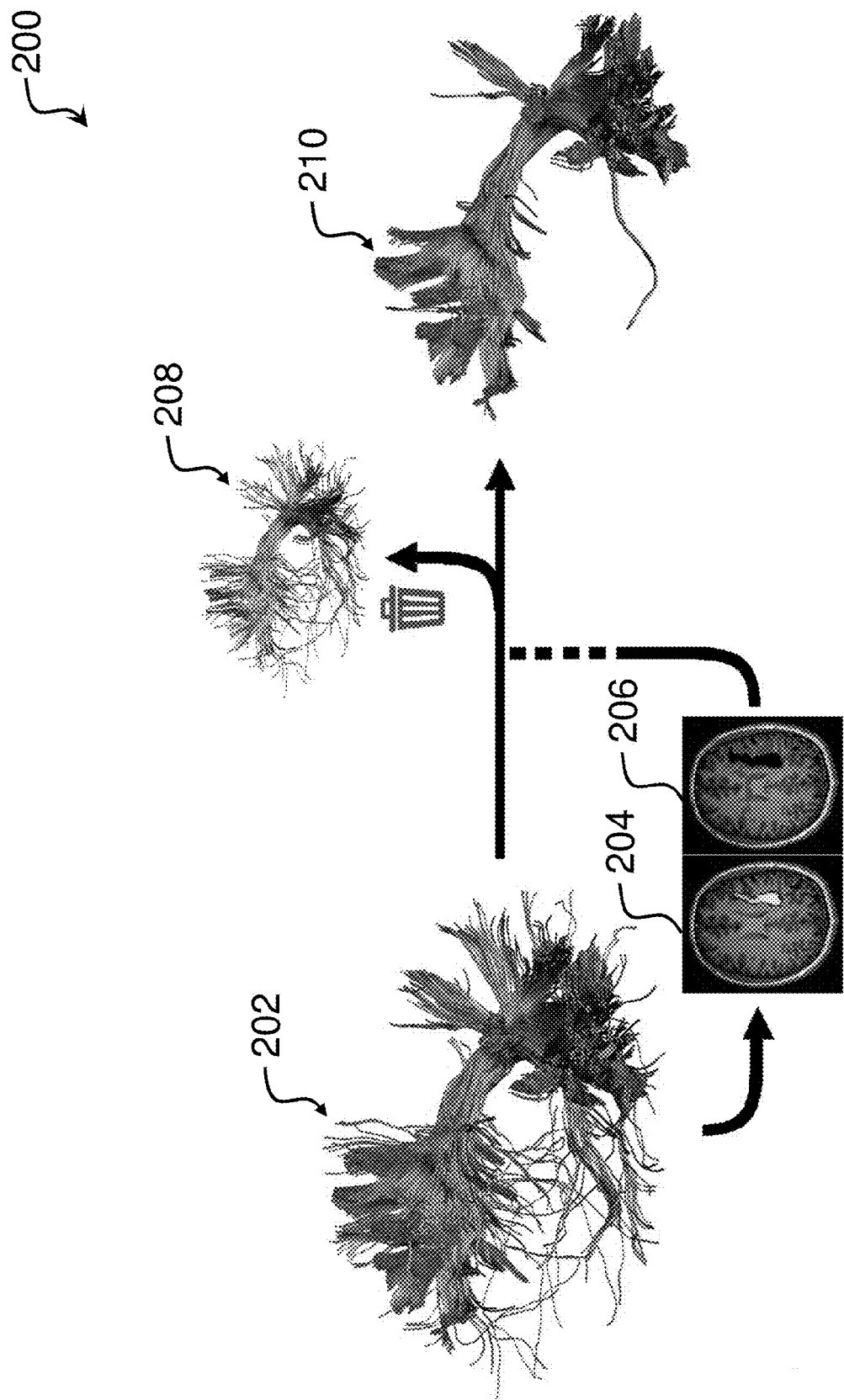
FIG. 2 is a process diagram for generating pruned tractograms of neural fiber bundles according to non-limiting embodiments.

Referring now to FIG. 2, shown is a process diagram depicting a topology-informed pruning (TIP) model according to non-limiting embodiments. The input data 202 are a set of trajectories (e.g., discrete curves of nerve fibers, also called tracts or traces) obtained from the tractogram of a target fiber bundle (e.g., set of nerve fibers). Tractography is a three-dimensional (3D) modeling technique used to visually represent nerve tracts using data collected by diffusion magnetic resonance imaging (MRI). The results are presented in two- or three-dimensional images called tractograms. Diffusion imaging with an MRI device produces in vivo magnetic resonance images of biological tissues sensitized with the local characteristics of molecular diffusion, e.g., water. The tractography of a fiber bundle can be obtained from a region-of-interest or any track selection approach. The number of trajectories should be high enough to produce a 3D histogram, e.g., as shown in a first density map 204. Density maps may be 2D or 3D visual representations of densities (e.g., number of item in an area) of neural fibers based on location in a fiber bundle. A 3D histogram may represent an intensity of a value (e.g., number of unique nerve fibers) on a 2D grid or plane. A tract may pass through the same voxel more than one time, but it is only counted once in the histogram. The second step is to identify voxels with a track count less than or equal to a threshold pruning value (e.g., a value of one) to generate a second density map 206. The threshold pruning value may be any value (e.g., one, two three, etc.) representative of a number of unique nerve tracts that, when a segment of a density map has a unique tract count less than or equal to the threshold pruning value, the segment likely contains one or more stray neural tracts or false connections, or no tracts at all. For example, the threshold pruning value may be one, and segments having a unique tract count of one may represent a segment containing a false connection. These voxels are nearby white matter regions where tracts "go astray" via an overlapping boundary. A set of tracts 208 are identified and excluded from the input data bundle 202 to produce a pruned tractogram 210 (e.g., a tractogram having one or more tracts removed from an initially generated tractogram). The whole process can be repeated until no more stray tracts are found. The computation complexity of TIP is O(N) (linear time complexity) where N is the number of trajectories. This TIP algorithm is fully automatic and requires no manual intervention to eliminate false connections.

Figure 3:
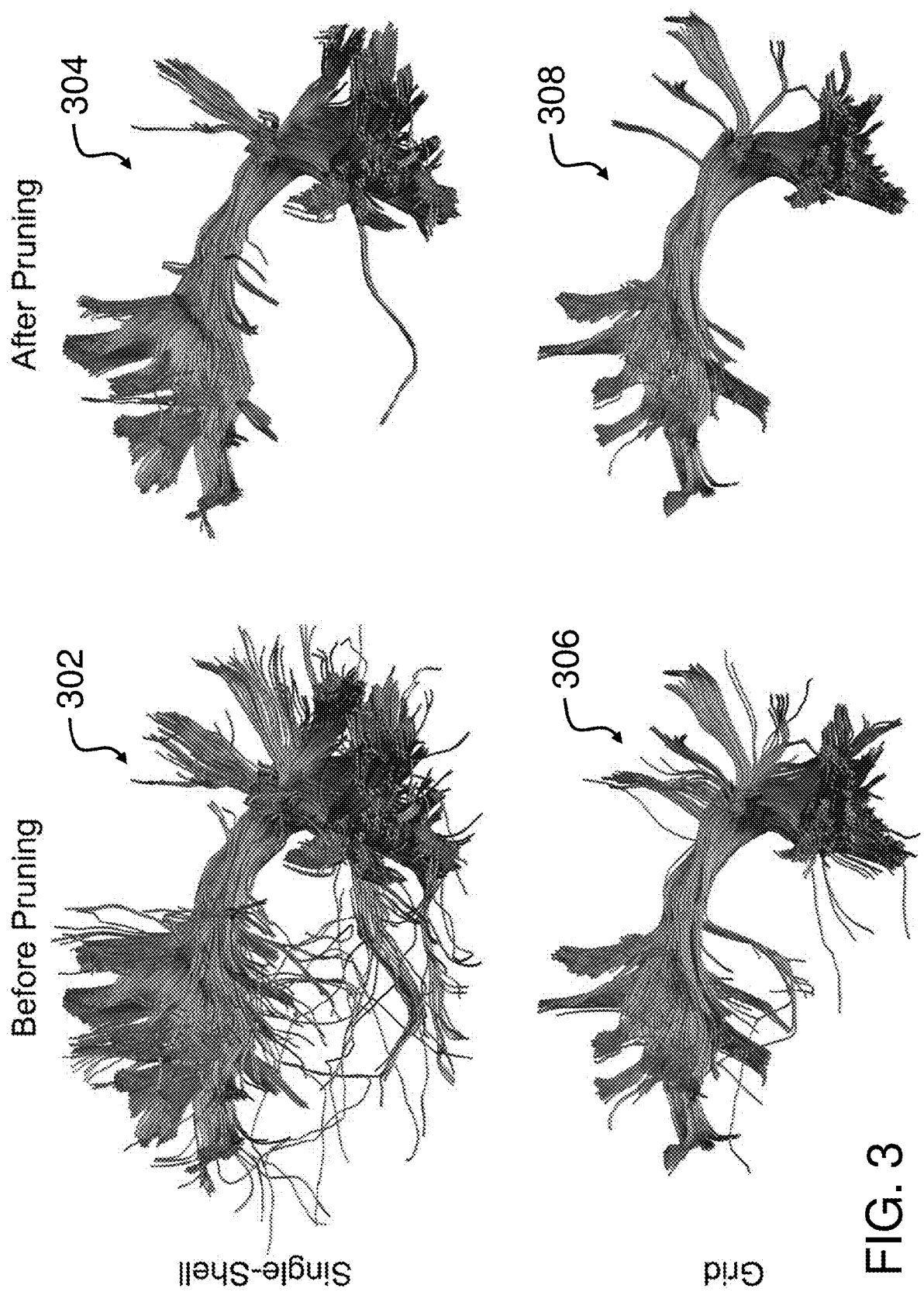
FIG. 3 is an input-output diagram for generating pruned tractograms of neural fiber bundles according to non-limiting embodiments.

Referring to FIG. 3, depicted is an input-output diagram depicting the topology-informed pruning (TIP) process according to non-limiting embodiments. Shown are tractograms of an evaluated 60-year-old female patient diagnosed with glioblastoma. The patient was scanned on a Siemens 3T Tim Trio scanner using a twice-refocused spin-echo diffusion sequence to acquire the diffusion data. A total of 514 diffusion directions were sampled with a maximum b-value of 7000 s/mm$^2$. The in-plane resolution was 2.4 mm. The slice thickness was 2.4 mm. The diffusion data were reconstructed using generalized q-sampling imaging with a diffusion sampling length ratio of 1.25. The restricted diffusion was quantified using restricted diffusion imaging to differentiate between tumor regions, edematous area, and normal white matter tissue. The tumor region and peritumoral edematous area were manually delineated to facilitate tracking the peritumoral fiber pathways. A peritumoral tractogram was generated using a deterministic fiber tracking algorithm with a region of interest placed at the peritumoral edematous region. A total of 10,000 tracts were calculated, and the tractograms with and without TIP were compared to examine whether TIP could improve quality.

With further reference to FIG. 3, depicted are tractograms of arcuate fasciculus before and after being pruned by the TIP algorithm. The tractogram generated using the angular gyms region-of-interest (ROI) method shows "noisy" fibers, especially using the single-shell scheme, shown in a first pre-pruning tractogram 302. The second pre-pruning tractogram 306 from the grid sampling scheme appears to be cleaner, but deviant trajectories are still visible. A first post-pruning tractogram 304 and second post-pruning tractogram 308 illustrate the removal of likely false connections by the TIP algorithm, to produce cleaner, more accurate tractograms. TIP effectively removes noisy fibers while retaining the main topology structure. The improvement is particularly striking in the single-shell scheme, as shown in the comparison of the first pre-pruning tractogram 302 relative to the first post-pruning tractogram 304. The pruned tractograms appear to be consistent with microdis section results.

Figure 4B:
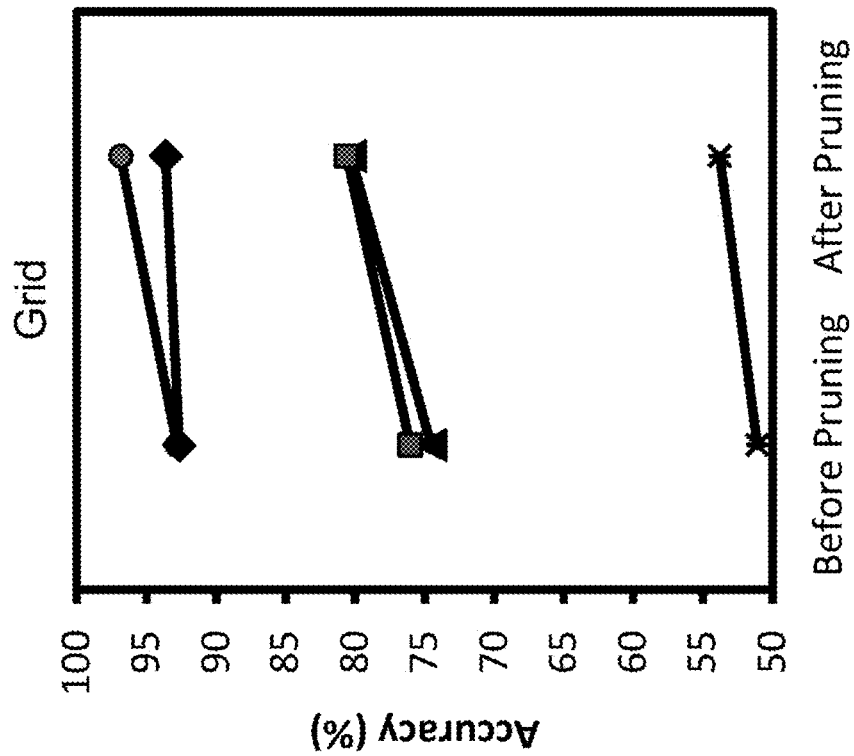
FIG. 4B illustrates evaluations of accuracy improvements provided by described systems and methods of generating pruned tractograms of neural fiber bundles according to non-limiting embodiments.
Figure 4A:
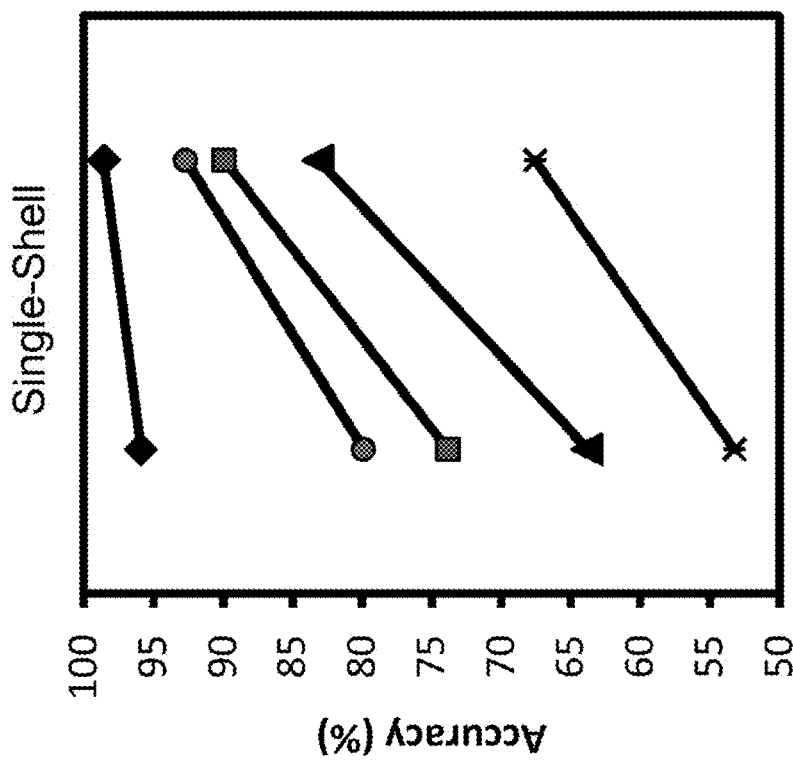
FIG. 4A illustrates evaluations of accuracy improvements provided by described systems and methods of generating pruned tractograms of neural fiber bundles according to non-limiting embodiments.

With reference to FIGS. 4A and 4B, depicted are evaluations of the accuracy improvements provided by described systems and methods of TIP according to non-limiting embodiments. The tractogram from a single-shell scheme is shown in FIG. 4A, whereas the tractogram from the grid scheme is shown in FIG. 4B. A total of 6 different evaluations were conducted independently by 6 neuroanatomists. The lines connect evaluations from the same neuroanatomists. In both FIG. 4A and FIG. 4B, all evaluations unanimously showed improved accuracy after TIP was applied to the arcuate fasciculus tractography. The average improvement in the single-shell scheme was 11.93%, whereas the average improvement in the grid scheme was 3.47%. Improvement is most obvious in the single-shell dataset. The lower improvement in the grid scheme could be due to its lower sensitivity for demonstrating branching fibers, as shown in the original tractogram before pruning, in FIG. 3.

Referring to FIG. 5, depicted are tractograms of arcuate fasciculus using the single-shell and grid schemes, comparing manual pruning by experts to computer-driven pruning by TIP, according to non-limiting embodiments. Depicted are tractograms produced when false tracts are removed by a representative expert (e.g., neuroanatomist), compared with the same tracts pruned by TIP. The neuroanatomist chosen for illustration had the highest diagnostic agreement with the other 5 neuroanatomists and thus can be viewed as the representative neuroanatomist of the group. In both the single-shell and grid schemes, the TIP-processed tractogram was highly consistent with the neuroanatomist-pruned tractogram, though differences can still be observed at minor branches. The first expert-pruned tractogram 502 is comparatively similar to the first TIP-processed tractogram 504, where a single-shell scheme was employed. The second expert-pruned tractogram 506 is comparatively similar to the second TIP-processed tractogram 508, where a grid scheme was employed.

Figure 6B:
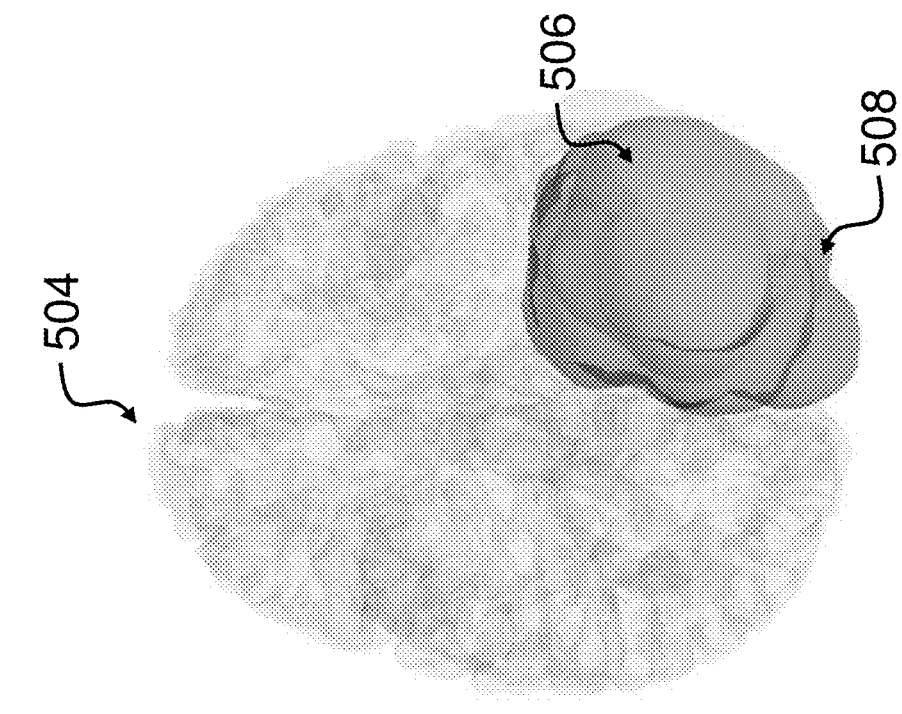
FIG. 6B illustrates a second step of a process for generating pruned tractograms of neural fiber bundles according to non-limiting embodiments.
Figure 6A:
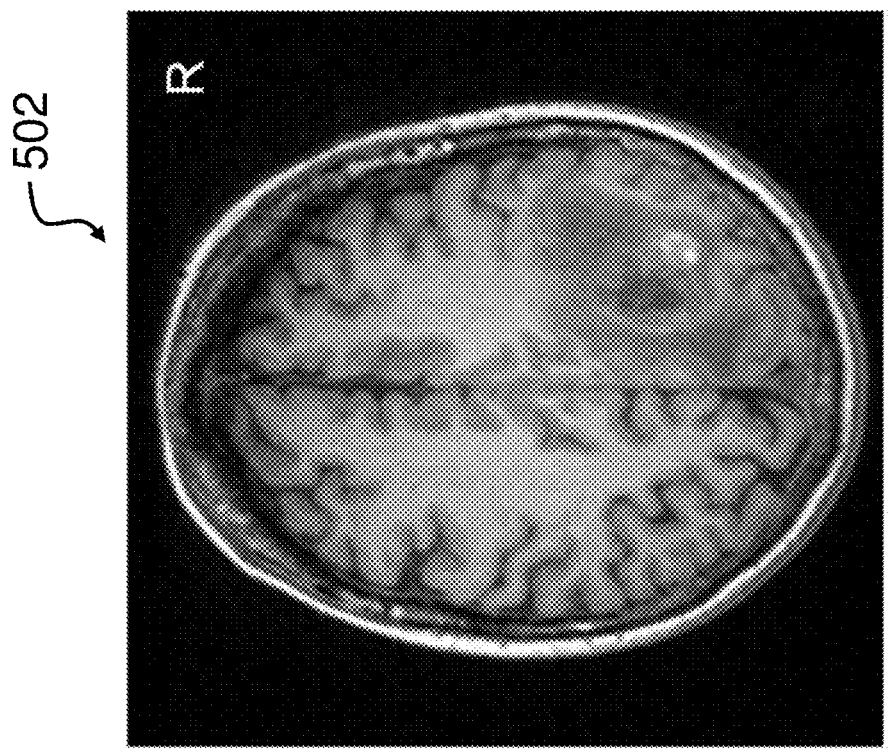
FIG. 6A illustrates a first step of a process for generating pruned tractograms of neural fiber bundles according to non-limiting embodiments.
Figure 7B:
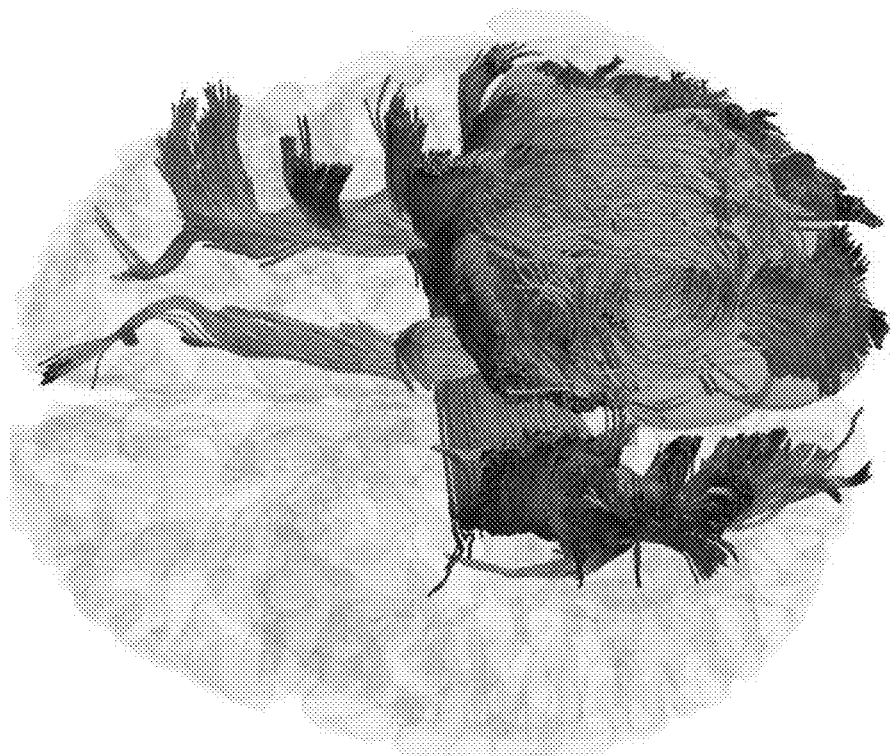
FIG. 7B illustrates a fourth step of a process for generating pruned tractograms of neural fiber bundles according to non-limiting embodiments.
Figure 7A:
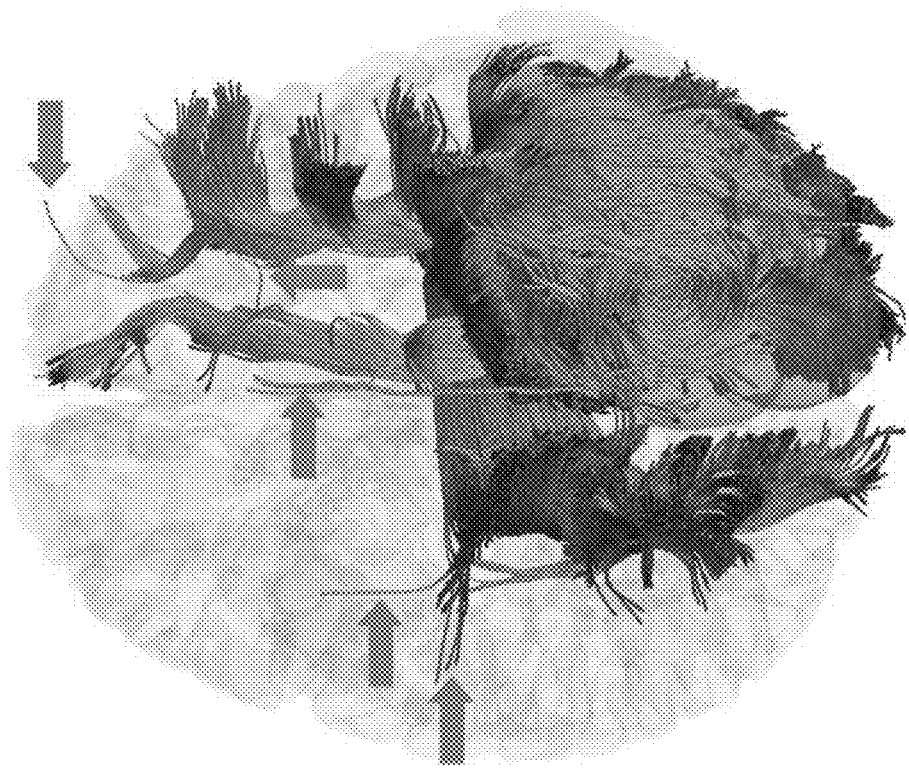
FIG. 7A illustrates a third step of a process for generating pruned tractograms of neural fiber bundles according to non-limiting embodiments.

Referring to FIGS. 6A, 6B, 7A, and 7B, depicted is a stepwise process illustrating how TIP can be used to remove false connections in peritumoral tractography according to non-limiting embodiments. Shown in FIG. 6A is the T1-weighted image 502 of a brain scan by MRI. Shown in FIG. 6B is a 3D reconstruction 504 depicting the tumor (flesh color, 506) located at frontoparietal region and its peritumoral edematous area (light-blue color, 508). FIG. 7A shows the peritumoral tractogram generated directly from the fiber tracking algorithm after placing the region of interest at the peritumoral edematous region. The red arrows point to possible false connections that cross the several sulci due to false continuity. These pathways are false connections because there should be no pathway crossing a sulcus between two nearby gyri. FIG. 7B shows the same tractogram processed automatically by two consecutive TIP runs to eliminate false connections. The false connections pointed by red arrows were eliminated without any manual invention, suggesting that TIP is an effective tool for improving the accuracy of diffusion MRI tractography.

Referring to FIG. 8, depicted is a system 800 for high-accuracy fiber tracking and eliminating false connections in tractograms, according to non-limiting embodiments. The system may include a magnetic resonance imaging (MRI) device 802 (e.g., an MRI machine) to acquire scan data (e.g., magnetic resonance image data) of at least a portion of a subject brain, e.g., a brain of a patient with a tumor, such as by diffusion magnetic resonance imaging. The MRI device 802 may communicate with a model processor 808 via a communication interface 804 (e.g., a local communication network, a cloud server system, a wired connection, and/or the like). Further disclosure of exemplary communication interfaces are described in connection with FIG. 9, in the context of a computing device. The model processor 808 may be a computing device programmed and/or configured to generate tractograms of neural fiber bundles, such as by executing a HAFT process. The model processor 808 may have a dedicated modeling engine 810 for generating tractograms from scan data of MRI devices 802. The scan data may be communicated to the model processor 808 via the communication interface 804. The scan data may also be separately acquired from the MRI device 802 and delivered to the model processor 808 via a data input port (e.g., internet port, USB port, serial port, etc.) of the computing device.

The system 800 may further include a neuronavigator 806. The neuronavigator 806 may be the same computing device comprising the model processor 808. The neuronavigator 806 may be programmed and/or configured to execute a computer-aided surgical process of the brain. The neuronavigator 806 may include a display 807 configured to show one or more tractograms of a scanned brain. The neuronavigator 806 may further include a graphical user interface (GUI) 809 for receiving input from a user, e.g., a neuroanalyst, a surgeon, and/or the like. The GUI 809 may be programmed and/or configured to display a tractogram and accept user input (e.g., identification, selection, etc.) of one or more neural tracts for removal from a displayed fiber bundle.

Figure 9:
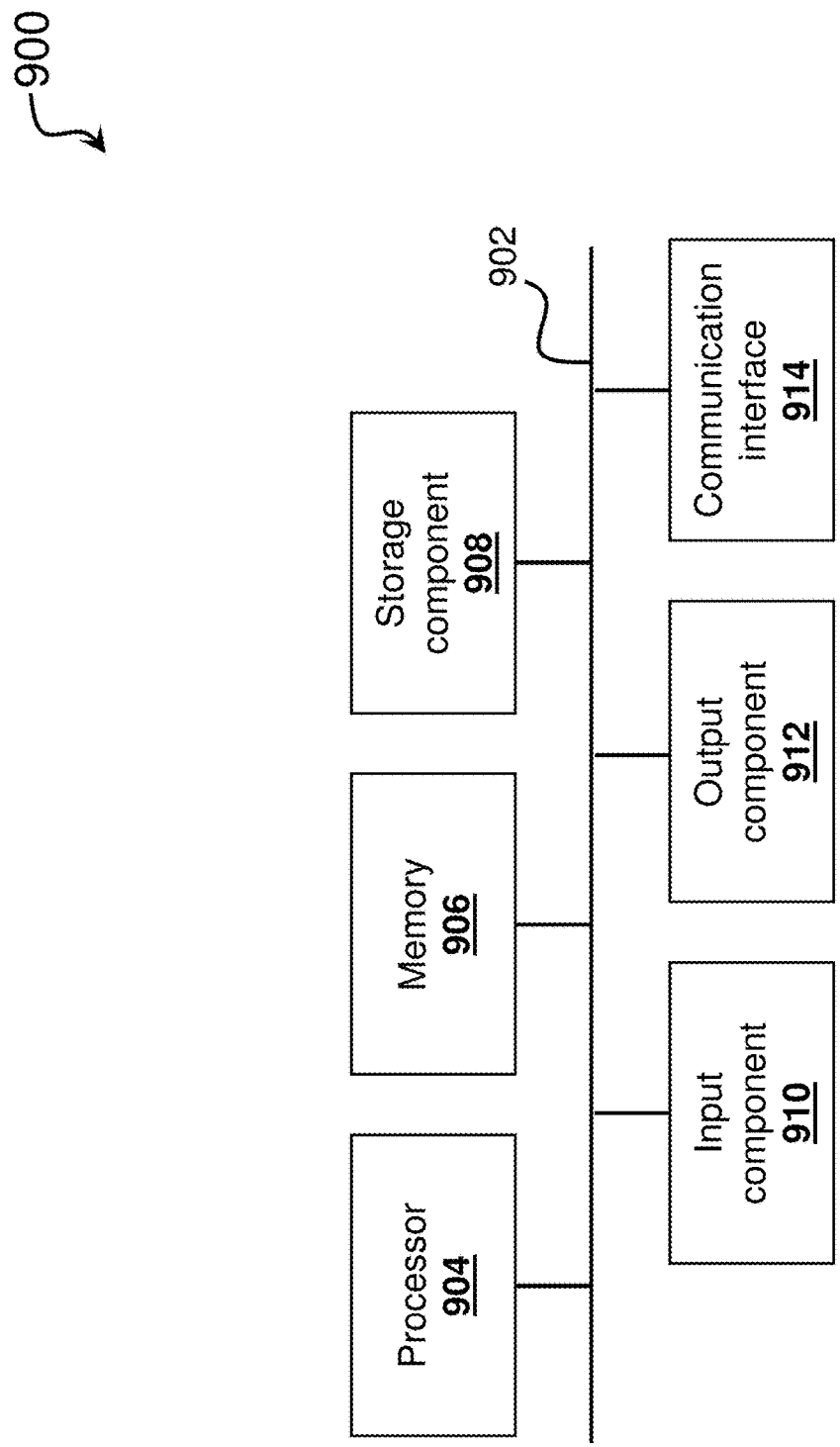
FIG. 9 illustrates example components of a device used in connection with non-limiting embodiments.

Referring now to FIG. 9, shown is a diagram of example components of a device 900 according to non-limiting embodiments. Device 900 may correspond to the MRI device 802, model processor 808, or neuronavigator 806 in FIG. 8, as an example. In some non-limiting embodiments, such systems or devices may include at least one device 900 and/or at least one component of device 900. The number and arrangement of components shown are provided as an example. In some non-limiting embodiments, device 900 may include additional components, fewer components, different components, or differently arranged components than those shown in FIG. 8. Additionally, or alternatively, a set of components (e.g., one or more components) of device 900 may perform one or more functions described as being performed by another set of components of device 900.

As shown in FIG. 9, device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 9, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Figure 10:
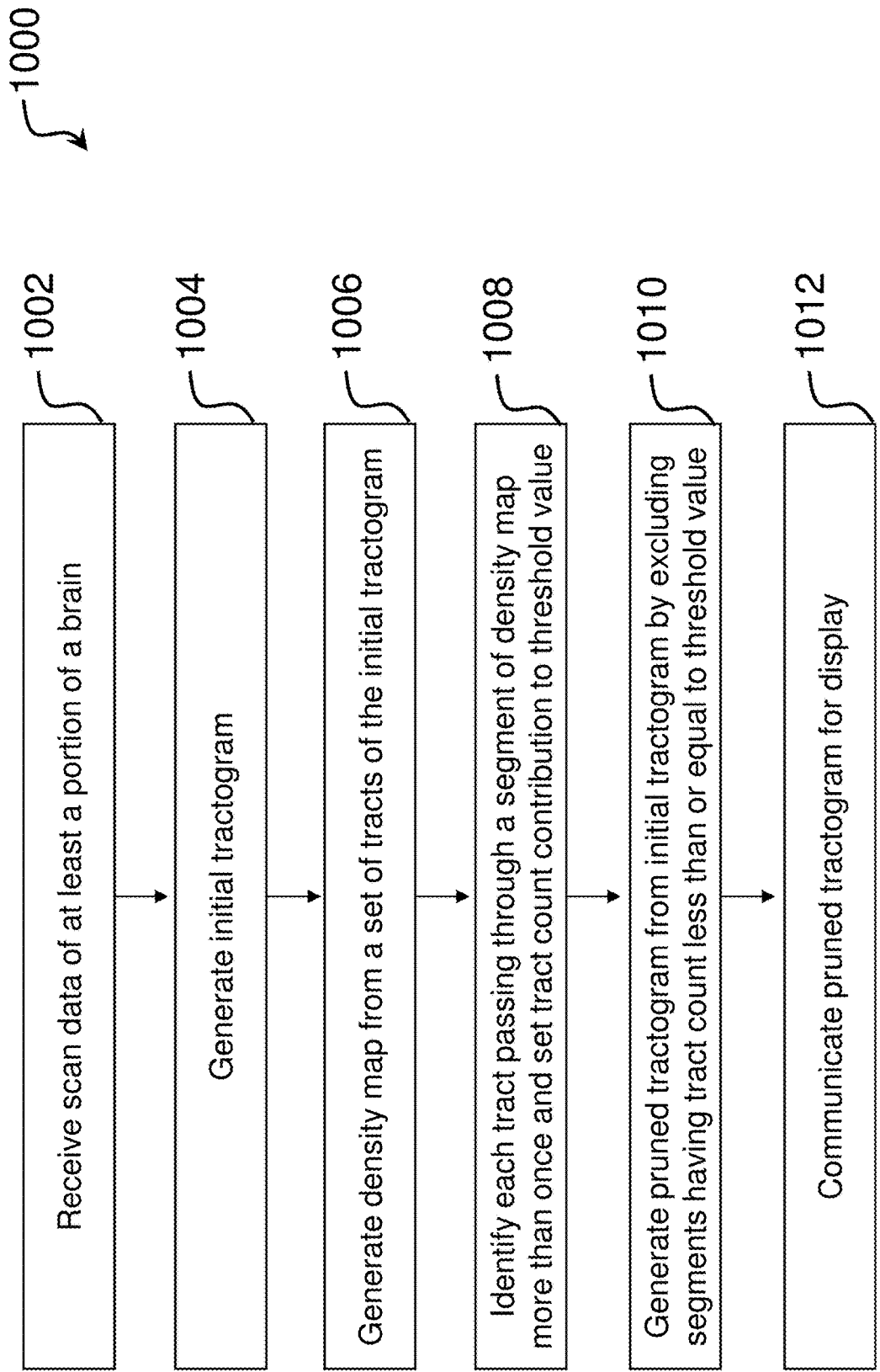
FIG. 10 is a process diagram of a system and method for generating pruned tractograms of neural fiber bundles according to non-limiting embodiments.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Referring to FIG. 10, depicted is a method 1000 of generating pruned tractograms of neural fiber bundles, according to non-limiting embodiments. One or more steps of the method 1000 may be executed by an MRI device 802, a model processor 808, and/or a neuronavigator 806. A computing device comprising one or more of an MRI device 802, a model processor 808, and/or a neuronavigator 806 may execute one or more steps of method 1000. In step 1002, a model processor may receive scan data (e.g., communicated from another computing device) produced by diffusion imaging of at least a portion of a brain from an MRI device. In step 1004, the model processor may generate an initial tractogram by mapping (e.g., tracing) neuronal fiber pathways (e.g., nerve fiber trajectories) of a target fiber bundle (e.g., set of neural fibers to be evaluated) of the scan data, such as by using a high accuracy fiber tracking (HAFT) process. In step 1006, the model processor may generate a density map of the scanned portion of the brain using a set of tracts from the initial tractogram. The set of tracts may be some or all of the tract from the initially generated tractogram.

In step 1008, the model processor may identify each tract that passes through a segment (e.g., two- or three-dimensional section, such as a unit of area by which a density map is constructed) of the density map more than once. The density map may be a three-dimensional (3D) histogram, and an evaluated segment may be a voxel (e.g., a unit of graphic information that defines a point in three-dimensional space). For each tract that passes through a same segment more than once, the tract's contribution to a unique tract count of the segment (e.g., the number of times counted in the total count) may be set to a threshold pruning value (e.g., one). For example, the model processor may identify a same tract passing through a particular voxel three times. Instead of the tract contributing to the tract count of the voxel three times, the contribution of the tract to the voxel's tract count may be set to one. In step 1010, the model processor may determine one or more segments having unique tract counts less than or equal to the threshold pruning value (e.g., one) and exclude the segment from the density map and corresponding evaluated tractogram. In doing so, the model processor may generate a pruned tractogram where one or more (or all) segments having unique tract counts of one or less are excluded from the tractogram. In step 1012, the model processor may communicate the pruned tractogram for display on a computing device (e.g., a neuronavigator).

Figure 11:
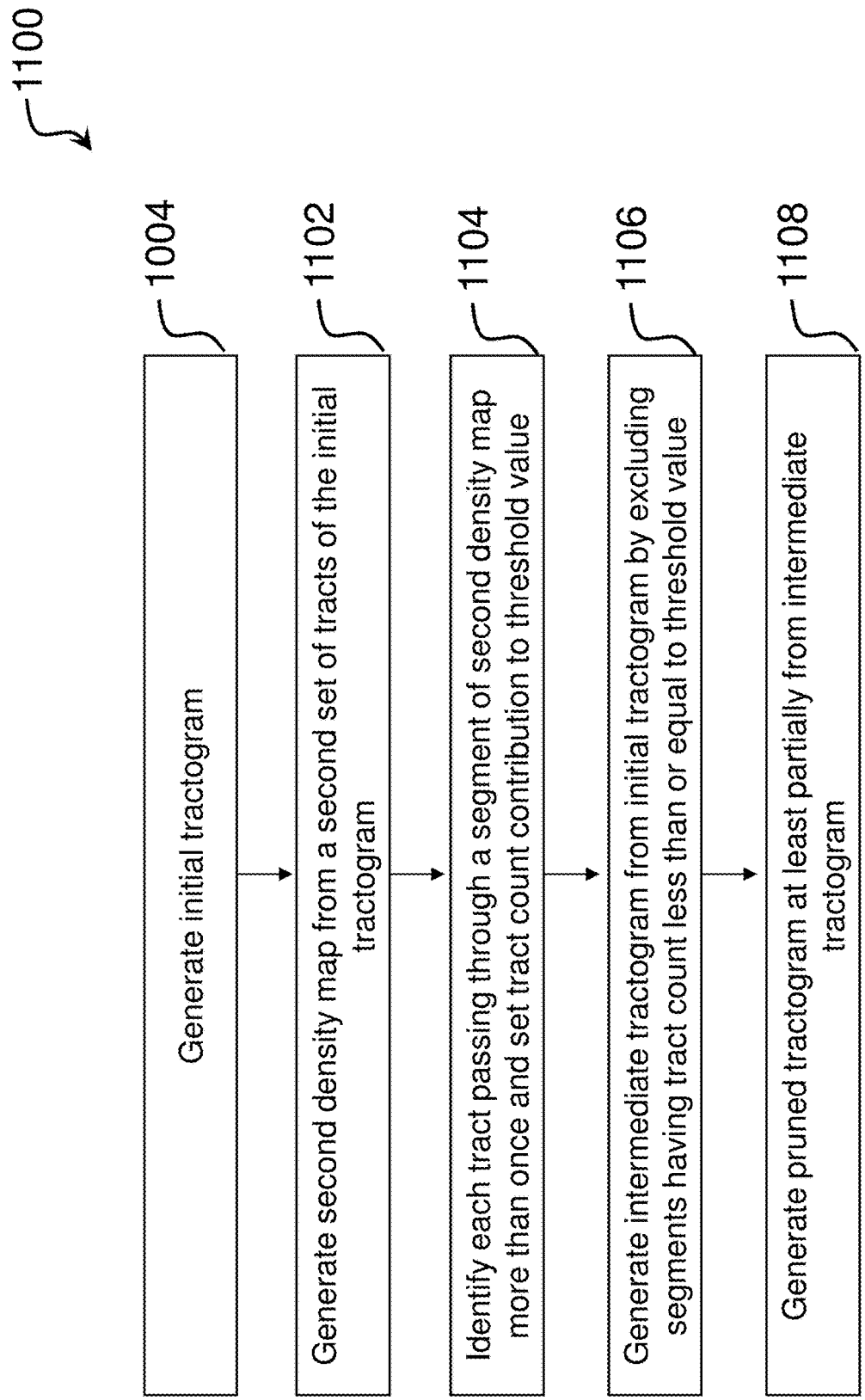
FIG. 11 is a process diagram of a system and method for generating pruned tractograms of neural fiber bundles according to non-limiting embodiments.

Referring to FIG. 11, depicted is a method 1100 of generating pruned tractograms of neural fiber bundles, according to non-limiting embodiments. One or more steps of the method 1100 may be executed by an MRI device 802, a model processor 808, and/or a neuronavigator 806. A computing device comprising one or more of an MRI device 802, a model processor 808, and/or a neuronavigator 806 may execute one or more steps of method 1100. Method 1100 illustrates the use of topology informed pruning (TIP) in multiple passes. In step 1004, a model processor may generate an initial tractogram by mapping neuronal fiber pathways of a target fiber bundle of the scan data, such as by using a HAFT process. In step 1102, the model processor may generate a second density map of at least a portion of the brain using a second set of tracts from the initial tractogram. The second set of tracts may be the same set of tracts used to generate the initial tractogram. In step 1104, the model processor may identify each tract that passes through a segment of the second density map more than once. The second density map may be a three-dimensional (3D) histogram, and an evaluated segment may be a voxel. For each tract that passes through a same segment more than once, the tract's contribution to a unique tract count of the segment (e.g., number of unique neural fiber trajectories passing through a segment) may be set to a threshold pruning value (e.g., one). For example, the model processor may identify a same tract passing through a particular voxel three times. Instead of the tract contributing to the tract count of the voxel three times, the contribution of the tract to the voxel's tract count may be set to one.

In step 1106, the model processor may determine one or more segments having unique tract counts less than or equal to the threshold pruning value (e.g., equal to one) and exclude the segment from the second density map and corresponding evaluated tractogram. In doing so, the model processor may generate a pruned tractogram where one or more (or all) segments having unique tract counts of the threshold pruning value or less are excluded from the tractogram. In step 1108, the final pruned tractogram may be generated based on pruning from the first density map of the initial tractogram and the second density map of an intermediate tractogram (e.g., exclude voxels pruned in the first or second pass). The second density map may exclude one or more pruned voxels from the first pass of the first density map. One or more intermediate tractograms may be produced to generate the final pruned tractogram (e.g., more than two passes of a TIP method may be employed).

Figure 12:
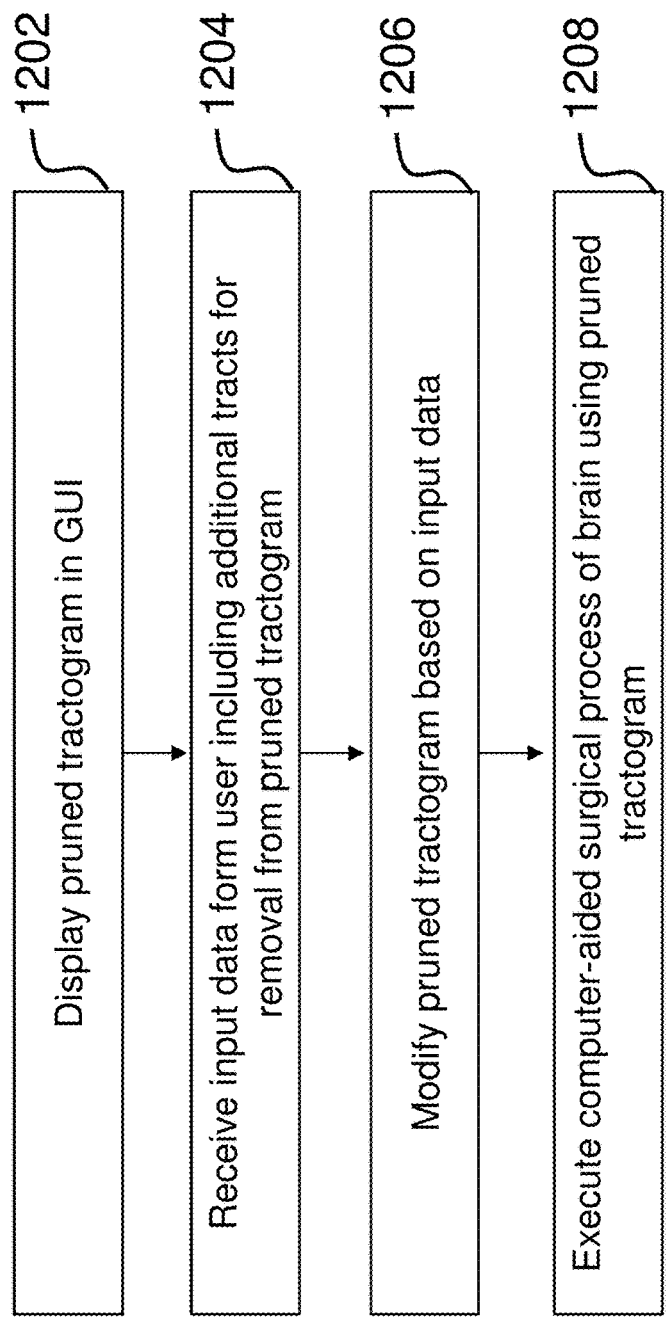
FIG. 12 is a process diagram of a system and method for generating pruned tractograms of neural fiber bundles according to non-limiting embodiments.

Referring to FIG. 12, depicted is a method 1200 of generating pruned tractograms of neural fiber bundles, according to non-limiting embodiments. One or more steps of the method 1200 may be executed by an MRI device 802, a model processor 808, and/or a neuronavigator 806. A computing device comprising one or more of an MRI device 802, a model processor 808, and/or a neuronavigator 806 may execute one or more steps of method 1200. In step 1202, a neuronavigator may display a pruned tractogram in a GUI. In step 1204, the neuronavigator may receive input data from a user including additional tracts for removal from the pruned tractogram. For example, a user may navigate a three-dimensional model of the pruned tractogram using computer controls and select one or more portions of fiber tracts for removal from the pruned tractogram. In doing so, the user (e.g., a neuroanalyst, a surgeon, etc.) may be presented with a pre-pruned tractogram, which may be critical in a time-sensitive procedure. The neuroanalyst may then focus on removing tracts that may have survived one or more TIP passes. In step 1206, the neuronavigator may modify the pruned tractogram based on the input data from the user. In step 1208, the neuronavigator may facilitate a computer-aided surgical process of the brain, using the pruned tractogram as a reference model of the patient's brain, to avoid affecting a critical neural pathway of the brain (e.g., neural pathways that, if removed, would result in a loss of function in the brain). Step 1208 may be executed after any version of a generated pruned tractogram is produced, such as after step 1010 or step 1012 in FIG. 10, after step 1108 in FIG. 11, and/or the like.

With further reference to the foregoing figures, it will be appreciated that changing parameter settings for the TIP algorithm could expand its potential applications. For example, the threshold for defining low-density voxels can be adjusted to adapt to a different seeding density. A high threshold will yield highly confirmative results to justify the existence of a fiber pathway. As more and more fiber tracking studies have been proposed to discover human brain pathways and their segmentation, TIP can strengthen the results by boosting the accuracy of tractography. The number of recursive iterations can be limited to a small number to allow for different pruning effects. For studies correlating structural connectivity with neuropsychological measures, a single iteration of TIP can complement group connectometry analysis to achieve better false discovery rates. In neurosurgical applications, TIP can assist mapping of peritumoral pathways to help neurosurgeons organize a detailed surgical plan.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A computer-implemented method comprising:
    receiving, with at least one processor, scan data produced by diffusion imaging of at least a portion of a brain from a magnetic-resonance imaging (MRI) device;
    generating, with the at least one processor, an initial tractogram by mapping neuronal fiber pathways of a target fiber bundle of the scan data;
    generating, with the at least one processor, a density map of the at least a portion of the brain using a set of tracts from the initial tractogram;
    identifying, with the at least one processor, each tract of the set of tracts that passes through a segment of a plurality of segments of the density map more than once, and setting a contribution of said tract to a unique tract count of the segment equal to a threshold pruning value;
    generating, with the at least one processor, a pruned tractogram from the initial tractogram by identifying at least one segment of the plurality of segments having a unique tract count less than or equal to the threshold pruning value and excluding the at least one segment from the pruned tractogram; and
    communicating, with the at least one processor, the pruned tractogram for display on a computing device,
    wherein the pruned tractogram comprises only voxels having unique tract counts greater than the threshold pruning value, and wherein the threshold pruning value is one.

2. The computer-implemented method of claim 1, wherein the computing device comprises a neuronavigator device programmed and/or configured to use the pruned tractogram in a computer-aided surgical process of the brain to avoid affecting a critical neural pathway of the brain.

3. The computer-implemented method of claim 1, wherein the density map is a three-dimensional (3D) histogram and the plurality of segments are a plurality of voxels of the 3D histogram.

4. The computer-implemented method of claim 1, further comprising:
    generating, with the at least one processor, a second density map of the at least a portion of the brain using a second set of tracts from the initial tractogram;
    identifying, with the at least one processor, each tract of the second set of tracts that passes through a segment of a plurality of segments of the second density map more than once, and setting a contribution of said tract to a unique tract count of the segment of the plurality of segments of the second density map equal to the threshold pruning value; and
    generating, with the at least one processor, an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram,
    wherein the pruned tractogram is generated at least partially from the intermediate tractogram.

5. The computer-implemented method of claim 1, further comprising:
    displaying, with the at least one processor, the pruned tractogram in a graphical user interface;
    receiving, with the at least one processor, input data from a user comprising additional tracts for removal from the pruned tractogram; and
    modifying, with the at least one processor, the pruned tractogram based on the input data.

6. The computer-implemented method of claim 5, wherein the computing device comprises a neuronavigator device programmed and/or configured to use the pruned tractogram in a computer-aided surgical process of the brain to avoid affecting a critical neural pathway of the brain.

7. A computer program product comprising at least one non-transitory computer-readable medium including program instructions that, when executed by at least one processor, cause the at least one processor to:
    receive scan data produced by diffusion imaging of at least a portion of a brain from a magnetic-resonance imaging (MRI) device;
    generate an initial tractogram by mapping neuronal fiber pathways of a target fiber bundle of the scan data;
    generate a density map of the at least a portion of the brain using a set of tracts from the initial tractogram;
    identify each tract of the set of tracts that passes through a segment of a plurality of segments of the density map more than once, and set a contribution of said tract to a unique tract count of the segment equal to a threshold pruning value;
    generate a pruned tractogram from the initial tractogram by identifying at least one segment of the plurality of segments having a unique tract count less than or equal to the threshold pruning value and excluding the at least one segment from the pruned tractogram; and
    communicate the pruned tractogram for display on a computing device,
    wherein the pruned tractogram comprises only voxels having unique tract counts greater than the threshold pruning value, and wherein the threshold pruning value is one.

8. The computer program product of claim 7, wherein the computing device comprises a neuronavigator device programmed and/or configured to use the pruned tractogram in a computer-aided surgical process of the brain to avoid affecting a critical neural pathway of the brain.

9. The computer program product of claim 7, wherein the density map is a three-dimensional (3D) histogram and the plurality of segments are a plurality of voxels of the 3D histogram.

10. The computer program product of claim 7, wherein the program instructions further cause the at least one processor to:

generate a second density map of the at least a portion of the brain using a second set of tracts from the initial tractogram;

identify each tract of the second set of tracts that passes through a segment of a plurality of segments of the second density map more than once, and setting a contribution of said tract to a unique tract count of the segment of the plurality of segments of the second density map equal to the threshold pruning value; and generate an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram, wherein the pruned tractogram is generated at least partially from the intermediate tractogram.

11. The computer program product of claim 7, wherein the program instructions further cause the at least one processor to:

display the pruned tractogram in a graphical user interface;

receive input data from a user comprising additional tracts for removal from the pruned tractogram; and modify the pruned tractogram based on the input data.

12. The computer program product of claim 11, wherein the computing device comprises a neuronavigator device programmed and/or configured to use the pruned tractogram in a computer-aided surgical process of the brain to avoid affecting a critical neural pathway of the brain.

13. A system comprising a neuronavigator device comprising a non-transitory computer-readable medium and at least one processor that is programmed and/or configured to:

receive scan data produced by diffusion imaging of at least a portion of a brain from a magnetic-resonance imaging (MRI) device;

generate an initial tractogram by mapping neuronal fiber pathways of a target fiber bundle of the scan data;

generate a density map of the at least a portion of the brain using a set of tracts from the initial tractogram;

identify each tract of the set of tracts that passes through a segment of a plurality of segments of the density map more than once, and set a contribution of said tract to a unique tract count of the segment equal to a threshold pruning value;

generate a pruned tractogram from the initial tractogram by identifying at least one segment of the plurality of segments having a unique tract count equal to the threshold pruning value and excluding the at least one segment from the pruned tractogram; and display the pruned tractogram, wherein the pruned tractogram comprises only voxels having unique tract counts greater than the threshold pruning value, and wherein the threshold pruning value is one.

14. The system of claim 13, wherein the at least one processor is further programmed and/or configured to use the pruned tractogram in a computer-aided surgical process of the brain to avoid affecting a critical neural pathway of the brain.

15. The system of claim 13, wherein the density map is a three-dimensional (3D) histogram and the plurality of segments are a plurality of voxels of the 3D histogram.

16. The system of claim 13, wherein the at least one processor is further programmed and/or configured to:

generate a second density map of the at least a portion of the brain using a second set of tracts from the initial tractogram;

identify each tract of the second set of tracts that passes through a segment of a plurality of segments of the second density map more than once, and setting a contribution of said tract to a unique tract count of the segment of the plurality of segments of the second density map equal to the threshold pruning value; and generate an intermediate tractogram from the initial tractogram by identifying at least one segment of the plurality of segments of the second density map having a unique tract count less than or equal to the threshold pruning value and excluding the at least one segment of the plurality of segments of the second density map from the intermediate tractogram, wherein the pruned tractogram is generated at least partially from the intermediate tractogram.

17. The system of claim 13, wherein the at least one processor is further programmed and/or configured to:

display the pruned tractogram in a graphical user interface;

receive input data from a user comprising additional tracts for removal from the pruned tractogram;

modify the pruned tractogram based on the input data; and use the pruned tractogram in a computer-aided surgical process of the brain to avoid affecting a critical neural pathway of the brain.

\* \* \* \* \*